United States Patent
Young et al.

(10) Patent No.: US 8,328,719 B2
(45) Date of Patent: Dec. 11, 2012

(54) METHOD OF INPUTTING DATA INTO AN ANALYTE TESTING DEVICE

(75) Inventors: Stanley Alan Young, North-Kessock (GB); David William Taylor, Alloa (GB); Allan Orr, Westhill (GB); Cheryl Neary, Boston, MA (US); Nicola Canning, Inverness (GB); Marc Daniel Stern, Morristown, NJ (US)

(73) Assignee: LifeScan Scotland Limited (GB)

( * ) Notice: Subject to any disclaimer, the term of this patent is extended or adjusted under 35 U.S.C. 154(b) by 0 days.

(21) Appl. No.: 13/178,236

(22) Filed: Jul. 7, 2011

(65) Prior Publication Data
US 2011/0263959 A1  Oct. 27, 2011

Related U.S. Application Data

(63) Continuation of application No. 11/719,460, filed as application No. PCT/US2005/047552 on Dec. 29, 2005, now Pat. No. 7,976,467.

(60) Provisional application No. 60/640,423, filed on Dec. 29, 2004.

(51) Int. Cl.
*A61B 5/00* (2006.01)
*G01N 33/48* (2006.01)
*G01N 21/75* (2006.01)
*G01D 1/00* (2006.01)
*G01N 31/00* (2006.01)
*G01N 33/52* (2006.01)

(52) U.S. Cl. ....... 600/365; 600/300; 600/583; 422/68.1; 422/400; 422/401; 422/402; 702/19; 702/22; 702/23; 702/30; 702/127

(58) Field of Classification Search .................... 600/365
See application file for complete search history.

(56) References Cited

U.S. PATENT DOCUMENTS
4,731,726 A   3/1988   Allen, III
(Continued)

FOREIGN PATENT DOCUMENTS
CN   1472536 A   2/2004
(Continued)

OTHER PUBLICATIONS

Accu-Chek Active Owner's Booklet, 2003, Roche Diagnostics, 54 pages.
(Continued)

*Primary Examiner* — In Suk Bullock
*Assistant Examiner* — Jennifer Wecker

(57) ABSTRACT

A meter is provided that includes an improved user interface that enables the user to take a specific action, leading them directly to data input options. Such a user interface could be used to input first selected information, such as whether a test was premeal or postmeal, immediately after receiving a result. Optionally, the user interface may include the ability to add an additional comment after inputting the first selected information. Provision of such a user interface would facilitate simpler capture of the first selected information each time the user performs a test, leading to an enhanced understanding of a patient's level of glycemic control. Designing a user interface to enable first selected information to be entered by a user directly after receiving a result is more likely to engage a patient by making it easy and simple to enter important information. This may enable capture of the information thought to be most pertinent e.g. premeal and postmeal information, enhancing the understanding by patients and their carers of the patient's control.

11 Claims, 9 Drawing Sheets

U.S. PATENT DOCUMENTS

| | | | |
|---|---|---|---|
| 5,251,126 | A | 10/1993 | Kahn et al. |
| 5,507,288 | A | 4/1996 | Bocker et al. |
| 6,656,114 | B1 | 12/2003 | Poulsen et al. |
| 2004/0044272 | A1 | 3/2004 | Moerman et al. |
| 2005/0022274 | A1 | 1/2005 | Campbell et al. |
| 2006/0010098 | A1 | 1/2006 | Goodnow et al. |
| 2007/0016449 | A1 | 1/2007 | Cohen et al. |
| 2008/0194987 | A1* | 8/2008 | Boecker .................. 600/583 |
| 2011/0178717 | A1 | 7/2011 | Goodnow et al. |

FOREIGN PATENT DOCUMENTS

| | | | |
|---|---|---|---|
| EP | 0320749 | A2 | 6/1989 |
| EP | 0483595 | | 5/1992 |
| EP | 0949506 | | 10/1999 |
| EP | 1346685 | A | 9/2003 |
| EP | 1369688 | A2 * | 12/2003 |
| GB | 2443434 | | 5/2008 |
| JP | 2000-055865 | | 2/2000 |
| JP | 2001-139844 | A | 5/2000 |
| JP | 2002-041654 | | 2/2002 |
| JP | 2004-139345 | | 5/2004 |
| WO | WO 97/08605 | A2 | 3/1997 |
| WO | WO 2004/005908 | A1 | 1/2004 |
| WO | WO 2004/023972 | A2 | 3/2004 |
| WO | WO 2005/011952 | A2 | 2/2005 |
| WO | WO 2005/093629 | A2 | 10/2005 |
| WO | WO 2006/037802 | A2 | 4/2006 |
| WO | WO 2008/060827 | A2 | 5/2008 |
| WO | WO 2008/106070 | A2 | 9/2008 |

OTHER PUBLICATIONS

Accu-Chek Advantage Owner's Booklet, 2004, Roche Diagnostics, 50 pages.
Accu-Chek Aviva Blood Glucose Meter Owner's Booklet, 2005, Roche Diagnostics, 78 pages.
Accu-Chek Compact Owner's Booklet, 2004 Roche Diagnostics, 54 pages.
Accu-Chek Complete Owner's Booklet, 2004 Roche Diagnostics, 101 pages.
Ascensia Breeze Blood Glucose Monitoring System User Guide, 2003 Bayer HealthCare LLC, 55 pages.
Ascensia Contour User Guide, 2003 Bayer HealthCare LLC, 46 pages.
Ascensia DEX2 Diabetes Care System User Guide, 2002 Bayer Corporation, 48 pages.
Ascensia Elite Diabetes Care System User Guide, 2002 Bayer Corporation, 51 pages.
Ascensia Elite XL Diabetes Care System User Guide, 2002 Bayer Corporation, 36 pages.
BD Latitude Diabetes Management System Owner's Guide, Becton Dickinson Canada Inc., 39 pages.
BD Logic Blood Glucose Monitor Owner's Guide, Becton Dickinson Canada Inc., 38 pages.
Tadashi Kuroyanagi, Portable Self-Control Device, Japanese Publication No. 2000-139844, published May 23, 2000, translated into English by IDEM translations, 22 pages.
One Touch Ultra Blood Glucose Monitoring System Owner's Booklet, LifeScan, Inc. 2002, 67 pages.
OneTouch UltraSmart Blood Glucose Monitoring System Meter and Electronic Logbook in One Owner's Booklet, OneTouch changes everything, 2002 LifeScan, Inc., 140 pages.
TheraSense FreeStyle Flash Blood Glucose Monitoring System Owner's Booklet, 2003 TheraSense, Inc., 35 pages.
TheraSense FreeStyle Blood Glucose Monitoring System Owner's Booklet, 2002 TheraSense, Inc., 68 pages.
Chinese Office Action, Chinese Patent application No. 200580048858.4, dated Mar. 6, 2008, 9 pages.

* cited by examiner

METHOD OF INPUTTING DATA INTO AN ANALYTE TESTING DEVICE

CROSS-REFERENCE TO RELATED APPLICATION

This application is a continuation filed under 35 USC §§120 of U.S. patent application Ser. No. 11/719,460, filed Dec. 29, 2005 which is now U.S. Pat. No. 7,976,467, which prior application Ser. No. 11/719,460 claims priority benefits under 35 USC §§120, 365 and 371 of International Application Number PCT/US2005/047552, filed on Dec. 29, 2005, which claims priority benefits under 35 USC §§119 and 120 to U.S. Provisional Application Ser. No. 60/640,423, filed on Dec. 29, 2004, and all prior applications are hereby incorporated by reference in their entireties into this application. The present invention is related to U.S. patent application Ser. No. 13/178,164, filed on Jul. 7, 2011.

FIELD OF THE INVENTION

This invention relates in general to an analyte measurement meter or system for measuring an analyte or indicator such as glucose in blood, interstitial fluid or urine, and more specifically relates to a method of using such a meter or system incorporating an improved user interface.

BACKGROUND OF THE INVENTION

Meters or devices for measuring an analyte or indicator, e.g. glucose, HbA1c, lactate, cholesterol, in a fluid such as a body fluid, e.g. blood, plasma, interstitial fluid (ISF), urine, typically make use of disposable test sensors. A test sensor that is specific for the analyte or indicator of interest may be inserted within a connector in the meter or system, or be delivered to a test location from within the meter or system. The test sensor becomes physically and electrically connected with a measuring circuit. A sample, for example blood, plasma, interstitial fluid (ISF) or urine, will typically contain numerous soluble or solubilized components, one of which will be the analyte or indicator of interest. An example user group that might benefit from the use of such a meter or system are those affected with diabetes and their health care providers.

Most conventional meters, such as blood glucose meters for example, enable the user to store the measurement values within an internal memory, along with the date and time at which each was taken. Such information is useful to the patient's healthcare practitioner (HCP) in prescribing a regiment for disease control, however capturing further information requires additional steps to be performed by the user and is typically overlooked.

Some meters such as the One Touch UltraSmart (available from LifeScan Inc., Milpitas, Calif.) allow several types of information related to exercise, health, medication and food for example, to be entered from one of four menu screens—the menu screens having first been selected from a result screen by a specific button.

SUMMARY OF THE INVENTION

A meter is provided that includes an improved user interface that enables the user to take a specific action, leading them directly to data input options. Such a user interface could be used to input first selected information, such as whether a test was premeal or postmeal, immediately after receiving a result. Optionally, the user interface may include the ability to add an additional comment after inputting the first selected information. Provision of such a user interface would facilitate simpler capture of the first selected information each time the user performs a test, leading to an enhanced understanding of a patient's level of glycemic control. Designing a user interface to enable first selected information to be entered by a user directly after receiving a result is more likely to engage a patient by making it easy and simple to enter important information. This may enable capture of the information thought to be most pertinent e.g. premeal and postmeal information, enhancing the understanding by patients and their carers of the patient's control.

DETAILED DESCRIPTION OF THE INVENTION

Figure 1:
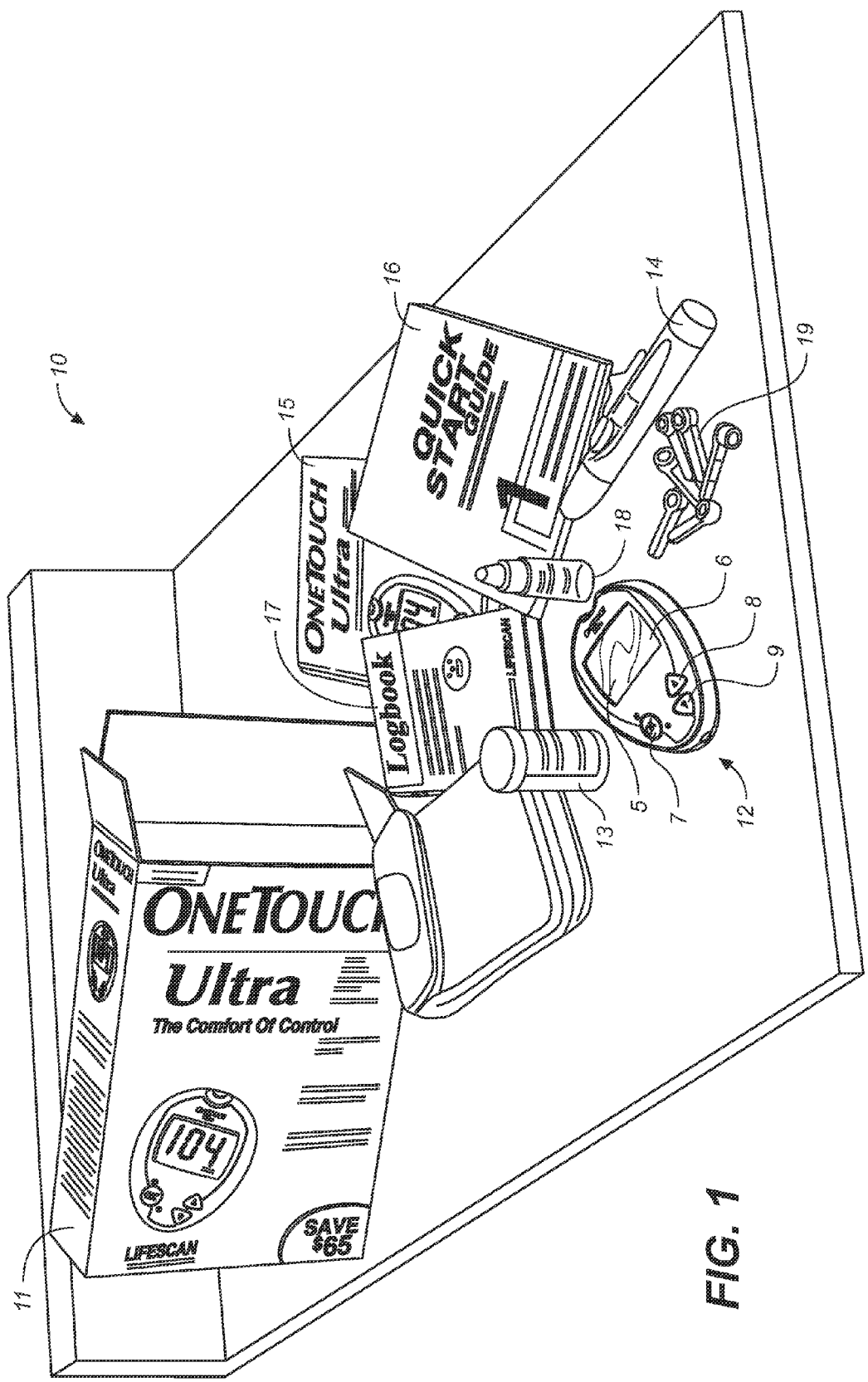
FIG. 1 is an illustration of a blood glucose monitoring system kit, according to an embodiment of the present invention.

FIG. 1 is an illustration of a blood glucose monitoring system kit 10, according to an embodiment of the present invention. Blood glucose monitoring system kit 10 includes a system box 11, a blood glucose meter 12, a vial of blood glucose test strips 13, a lancing device 14, instructions for use 15, a quick start guide 16, a written log book 17, a bottle of control solution 18, and a number of lancets 19. Blood glucose meter 12 includes a display 6, an OK button 7, an UP button 8, a DOWN button 9 and a display backlight 5.

FIG. 1 shows an example blood glucose monitoring test kit 10 that would typically be provided to patients who are required to test their blood glucose concentration regularly. Such kits conventionally contain a user guide 15 as well as a quick start guide 16, and also a logbook 17. Patients are encouraged to note down details regarding their test results and also capture other information about how they are generally feeling, with an aim to better understand the impact of circumstances such as meals, exercise, illness etc. on their blood glucose. However, many users may find it inconvenient to carry additional items such as logbook 17, and therefore not capture this information that may be potentially useful to their physicians.

As illustrated in FIG. 1, OK button 7 is located on the front of blood glucose meter 12. OK button 7 has many functions: it is used to turn blood glucose meter 12 on and off; it is used to turn display backlight 5 on or off; it is used to select items from various menus, as outlined in the following figures; and it is used when changing the batteries for blood glucose meter 12. Various functions are activated, depending upon how long OK button 7 is held down. For instance, when blood glucose meter 12 is off, it can be turned on by holding OK button 7 down for approximately 3 seconds. It can be turned off by holding OK button 7 down for approximately 5 seconds. Display backlight 5 can be turned on, when blood glucose meter 12 is on, by holding OK button 7 down for approximately 3 seconds. Display backlight 5 can be turned off by holding OK button 7 down for approximately 2 seconds. Items can be selected from various menus by holding OK button 7 down for less than approximately 3 seconds. Blood glucose meter 12 can be prepared for new batteries by holding OK button 7 down for approximately 2 seconds before new batteries are installed. The times mentioned are approximate, and can be varied to help distinguish between functions.

Figure 2:
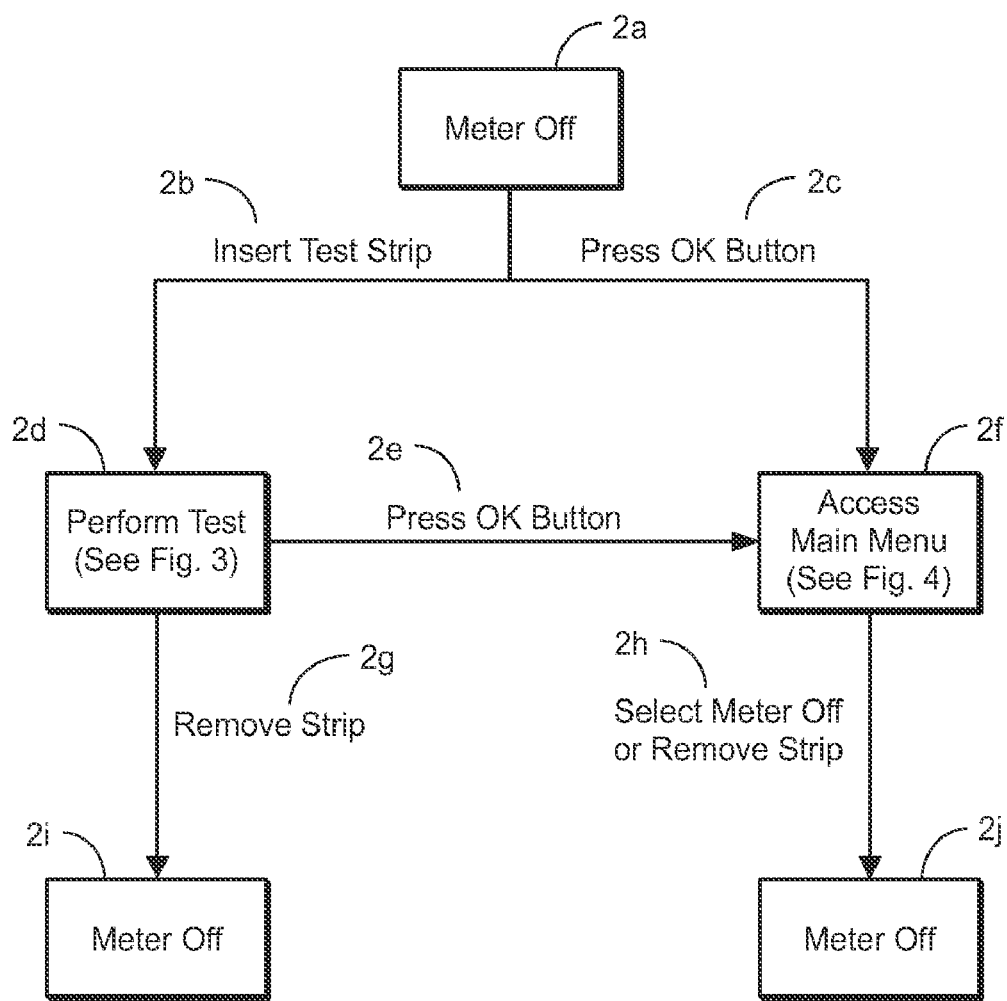
FIG. 2 is a first flow sheet that illustrates a user interface for a blood glucose meter, according to an embodiment of the present invention.
Figure 3:
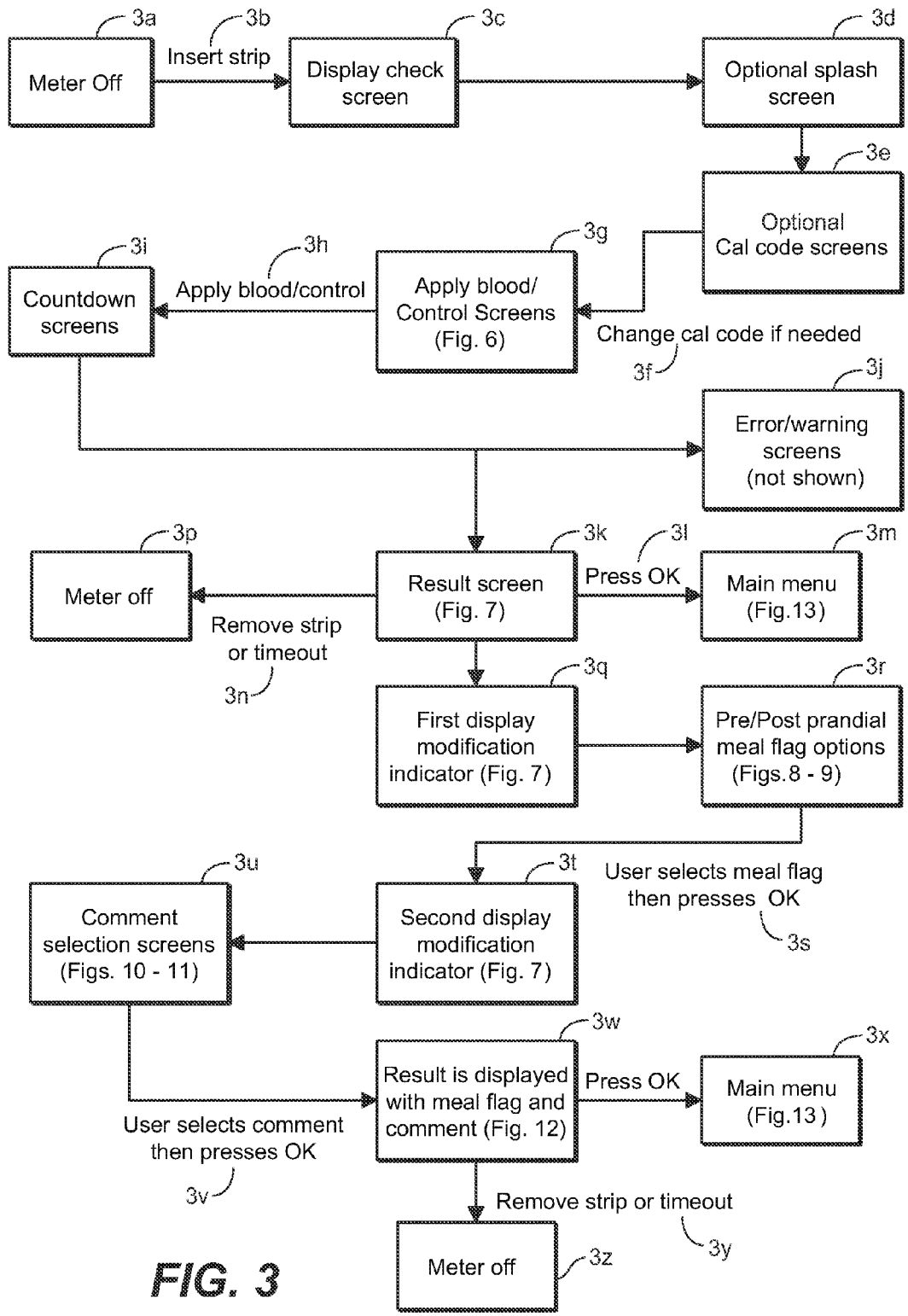
FIG. 3 is a second flow sheet that illustrates a user interface for a blood glucose meter, according to an embodiment of the present invention.
Figure 4:
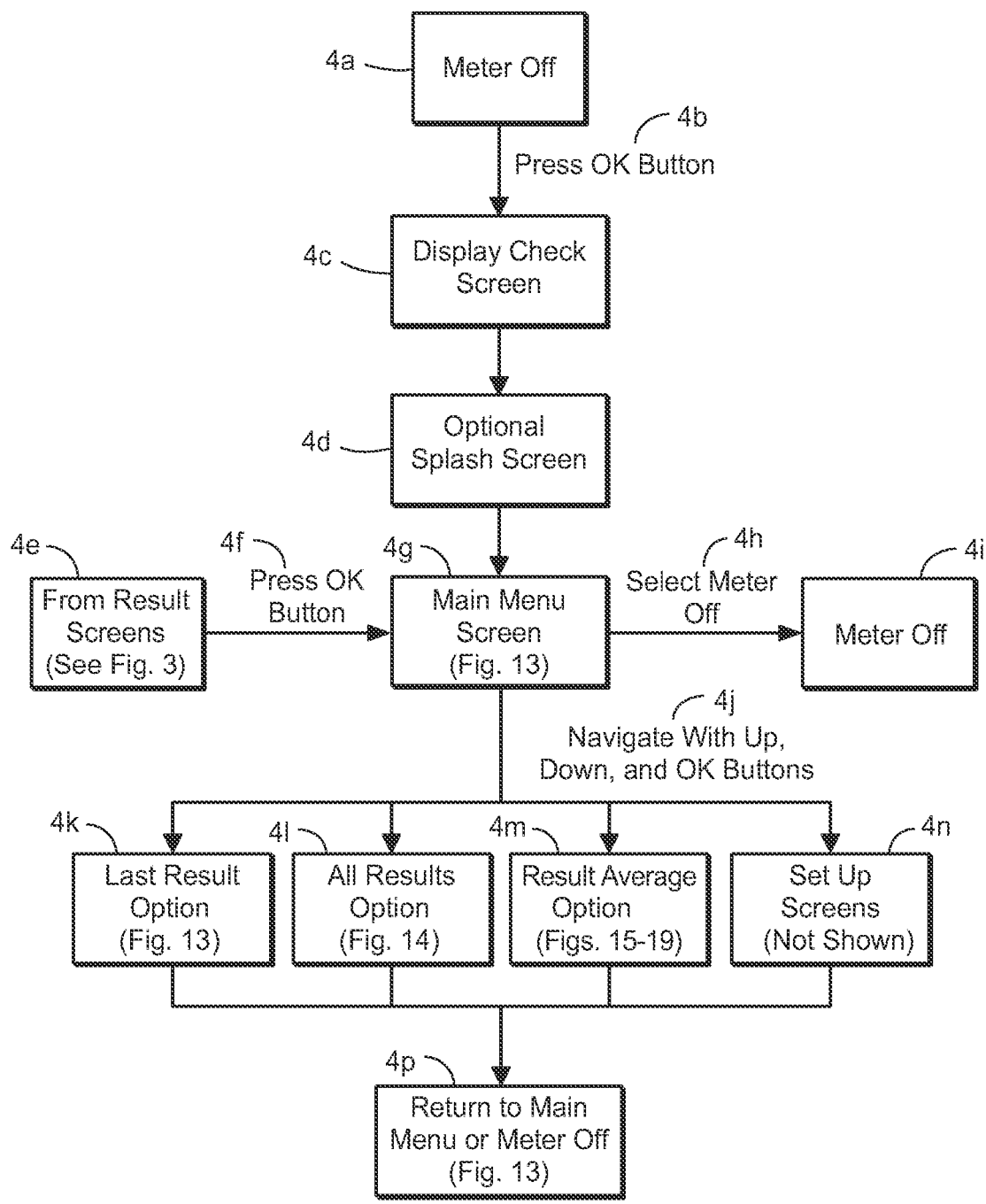
FIG. 4 is a third flow sheet that illustrates a user interface for a blood glucose meter, according to an embodiment of the present invention.

An envisioned user interface for blood glucose meter 12 is illustrated in the following figures. FIGS. 2, 3, and 4 illustrate the user interface with flow diagrams, while the remaining figures provide more detailed description. In FIGS. 2, 3, and 4, text that is not in a box represents an action performed by the user, while text within boxes represents the results of said actions.

As illustrated in FIG. 2, the interface begins with meter 12 in an off mode 2a. With the meter in off mode 2a, the user has two options. The first option is to insert a test strip 2b, while the second option is to press OK button 2c. Presenting the user with only two options simplifies the user interface, and makes it easy to use. To activate the meter, a user either inserts a strip or presses the OK button. This is much simpler than the protocols used in existing blood glucose meters. To perform a test, a strip is inserted. To process data, the OK button is pressed.

Referring to FIG. 2, if a user chooses the first option (inserting a test strip 2b), the perform test mode 2d is reached. This mode is described in detail in FIG. 3, and in subsequent figures. While in the perform test mode 2d, the meter can be returned to an off mode 2i by either removing the test strip 2g, or allowing the meter to timeout. From any mode, after 2 minutes of inactivity, the meter will automatically return to an off mode. This is referred to as a timeout.

If a user chooses the second option (pressing OK button 2c in FIG. 2), main menu mode 2f is reached, and will be described in more detail in relation to FIG. 4. While in main menu mode 2f, meter 12 can be returned to an off mode 2j by selecting meter off from the main menu, by removing the test strip, or by allowing the meter to timeout 2h.

Figure 6:
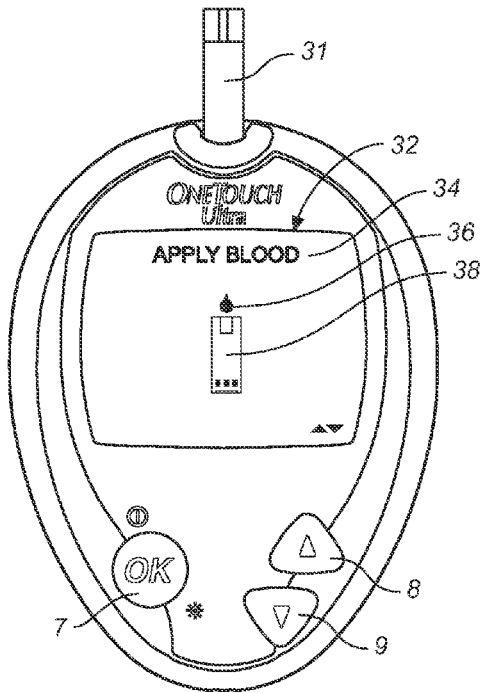
FIG. 6 is an illustration of an apply blood screen for a blood glucose meter, according to an embodiment of the present invention.
Figure 7:
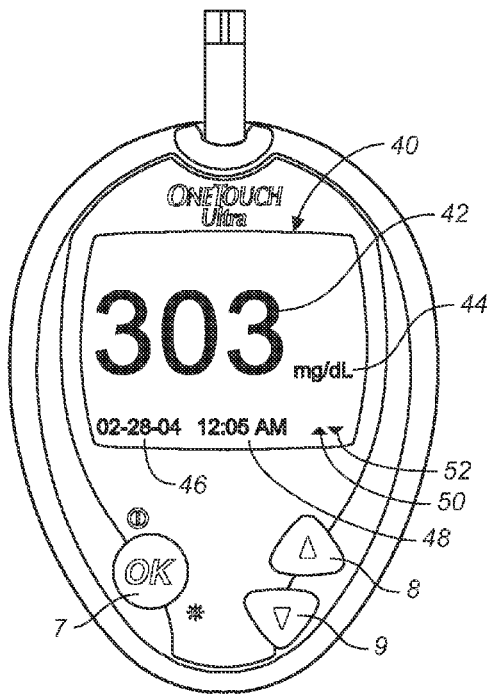
FIG. 7 is an illustration of a test result screen for a blood glucose meter, according to an embodiment of the present invention.

Referring now to FIG. 3, the perform test mode is illustrated in greater detail. From a meter off mode 3a, a strip is inserted 3b activating the meter. A display check screen 3c, a splash screen 3d and a cal code screen 3e (not shown) may optionally be displayed along with confirmation of the calibration code 3f, prior to display of the 'apply blood' (and optionally control solution) screen 3g. The apply blood screen is illustrated in FIG. 6. If the user presses up button 8 at this point, 'apply control' would appear in place of 'apply blood'. After applying blood or control 3h, a series of countdown screens 3i may be displayed, followed by either a result screen 3k or an error or warning screen 3j (not shown). An example results screen is illustrated in FIG. 7. From result screen 3k, the meter can be returned to an off mode 3p by removing the test strip or waiting for the meter to timeout 3n.

Figure 9:
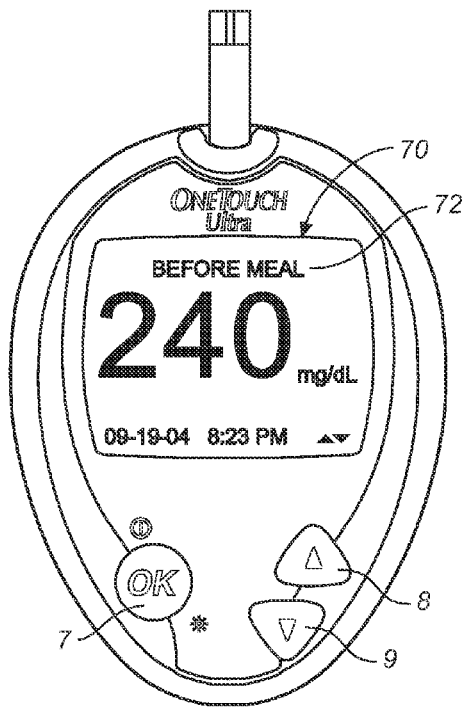
FIG. 9 is an illustration of a before meal result screen for a blood glucose meter, according to an embodiment of the present invention.
Figure 10:
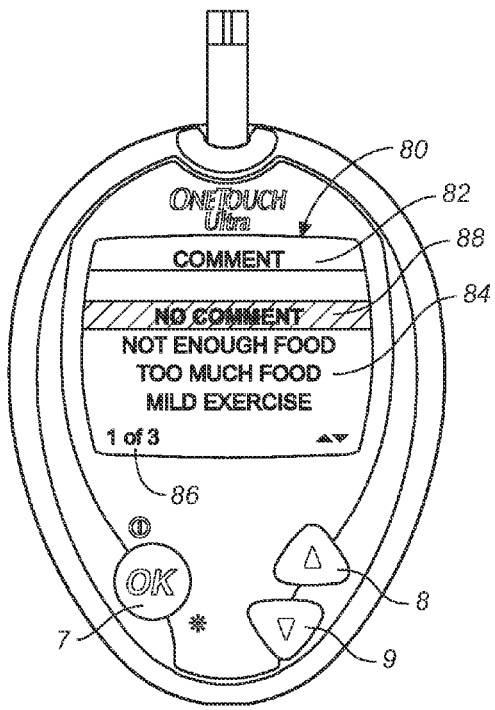
FIG. 10 is an illustration of a first comment selection screen for a blood glucose meter, according to an embodiment of the present invention.
Figure 11:
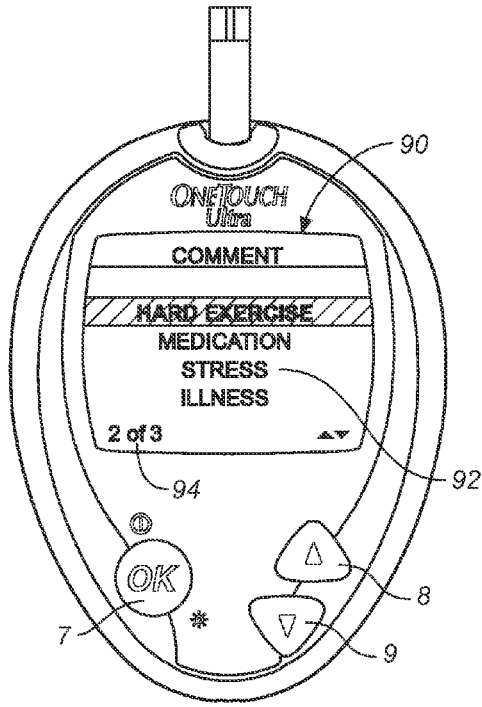
FIG. 11 is an illustration of a second comment selection screen for a blood glucose meter, according to an embodiment of the present invention.
Figure 12:
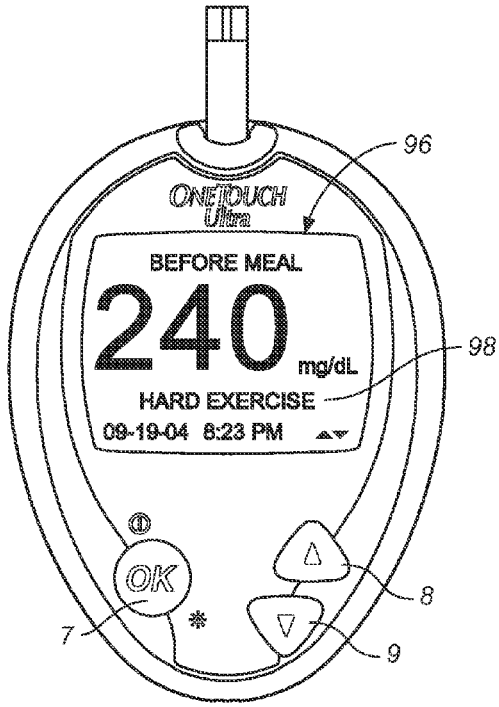
FIG. 12 is an illustration of a result screen for a blood glucose meter according to an embodiment of the present invention, including a meal flag and comment.

In an embodiment of the present invention, the user may be presented with a first display modification indicator 3q (such as for example item 50 in FIG. 7). Such a display modification indicator could, for example, flash on and off to prompt the user to take a specific action e.g. press a certain button. In this example embodiment, if the user follows the prompt e.g. by pressing the up button 8 as directed by flashing arrow 50, they are led directly to an input for premeal or postmeal flag 3r, as will be described further in relation to FIGS. 8 and 9. The user then chooses either a pre- or post meal flag and presses OK 3s to return to result screen 3k. The user may then be presented with a second display modification indicator 3t, again prompting them towards a specific action such as pressing a particular button. In this example embodiment, a down arrow icon (item 52 in FIG. 7) may flash on and off, prompting the user to press down button 9. This action takes the user directly to comment selection screens 3u as shown in FIGS. 10 to 12, whereby they are prompted to enter a comment relative to their recent activity or health state 3v. Once selected by pressing OK button 7, the display returns to a result screen that includes both the meal flag and comment information 3w, as shown in FIG. 12. Once a meal flag and/or comment has been entered, the meter can be returned to an off mode 3z by either removing the test strip or waiting for the meter to timeout 3y.

Figure 13:
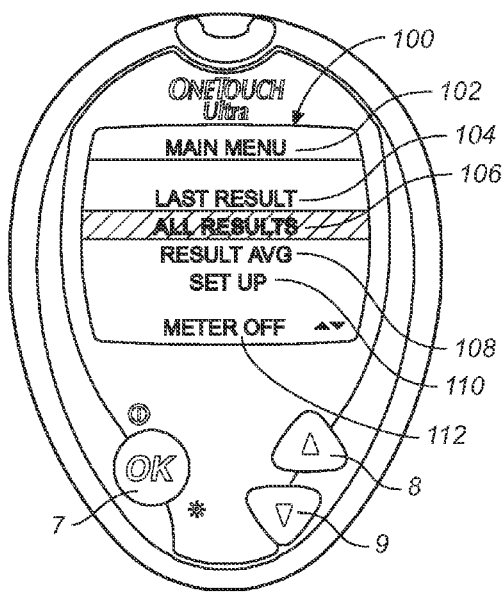
FIG. 13 is an illustration of a main menu screen for a blood glucose meter according to an embodiment of the present invention, with an 'all results' option highlighted.

A third option while the initial result screen 3k is displayed is to press the OK button 7 (step 3l), which leads to the main menu mode 3m, illustrated in FIG. 13. Removing the test strip, selecting meter off from the main menu, or waiting for the meter to timeout returns the meter to an off mode 3z.

Referring now to FIG. 4, an example main menu will be described in more detail. From a meter off mode 4a, OK button 7 is pressed 4b, activating the meter. A display check screen 4c and a splash screen 4d are then optionally displayed, prior to a main menu 4g being displayed, as shown in FIG. 13. Main menu screen 4g can also be reached from the result screens 4e by pressing the OK button 4f. This was illustrated in steps 3k, 3l and 3m of FIG. 3.

While at main menu screen 4g, the up and down buttons (buttons 8 and 9 respectively) can be used 4j to display a 'last result' option 4k, an 'all results' option 4l, a 'result average' option 4m and a 'setup' option 4n. Options 4k, 4l, 4m and 4n are shown in FIG. 13, and result average screens 4m are illustrated in FIGS. 15 through 19.

From the last result screens 4k, the all results screens 4l, the result average screens 4m, or the setup screens 4n, the display can be returned to the main menu screen 4g or off mode 4p by selecting the main menu or meter off options. From main menu screen 4g, the meter can be returned to an off mode 4i by selecting the meter off option 4h, or letting the meter timeout.

After turning the meter on, either by inserting a test strip or pressing OK button 7, all pixel elements of display 6 may be turned on for a few seconds, producing a dark screen. Missing pixel elements would be seen as light areas against the dark background, used to diagnose pixel failure. After display check screen 4c, a splash screen 4d may optionally be displayed, optionally including product identification and/or a copyright statement. The appearance of a splash screen may vary from one model of meter to another, or may be omitted altogether.

Figure 5:
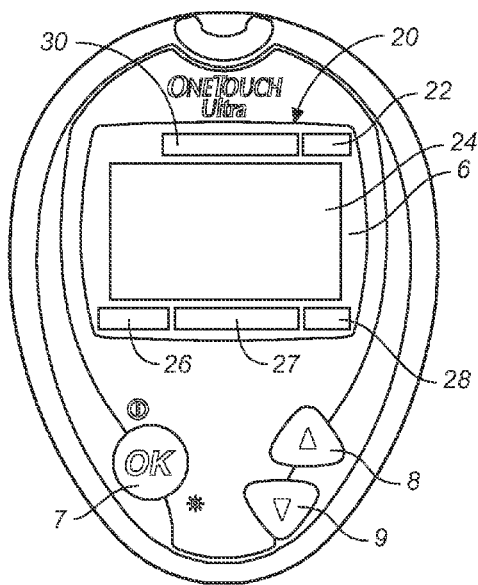
FIG. 5 is an illustration of a screen layout for a blood glucose meter, according to an embodiment of the present invention.

FIG. 5 shows an embodiment of a screen layout 20 for display 6 of meter 12. Screen layout 20 includes a heading area 30, a battery icon area 22, a data display area 24, a page number area 26, a footer area 27, and a navigation indicator area 28. Heading area 30 is used to display screen titles and meal flags. Battery icon area 22 is used to display a battery status icon. Data display area 24 is used to display menu options, warning messages, and test results. Page number area 26 is used to display page numbers when screens are split into multiple pages. Footer area 27 is used to display selectable navigation options. Navigation indicator area 28 is used in one embodiment of this invention to display arrow icons. Such arrow icons may be used to prompt or remind the user that further options are accessible, and take them directly to data input screens as described in relation to FIG. 3.

When entering the test mode, a calibration code screen may optionally be displayed to the user. After ensuring that the meter has the correct calibration code 3f (if required), the 'apply blood' screen 32 is presented to the user, an example of which is provided in FIG. 6. Apply blood screen 32 includes a 'apply blood' title 34, a blinking drop icon 36 and a test strip icon 38. Blinking drop icon 36 appears and disappears in apply blood screen 32, attracting the attention of the user. If up button 8 is pressed, or optionally down button 9, 'apply blood' title 34 changes to 'apply control' solution (not shown). To analyze a blood sample, the user applies blood to test strip 31 while apply blood screen 32 is displayed. Similarly, to perform a control solution test, the user applies control solution to test strip 31 when the 'apply control solution' screen is displayed. Each time meter 12 is turned on, the 'apply blood' screen 32 is displayed by default, with access to the 'apply control solution' screen requiring the user to press a button while 'apply blood' screen 32 is displayed.

After application of sample or control solution to test strip 31, a series of countdown screens may optionally be displayed (not shown) while the meter calculates the blood glucose concentration. Countdown screens provide the user with a sense of the time remaining before the result will be displayed. Following the countdown, a test result screen 40 is displayed, as illustrated in FIG. 7. Test result screen 40 includes a test result 42, a unit of measurement 44, a test date 46, a test time 48, a first display modification indicator 50 and a second display modification indicator 52.

Figure 8:
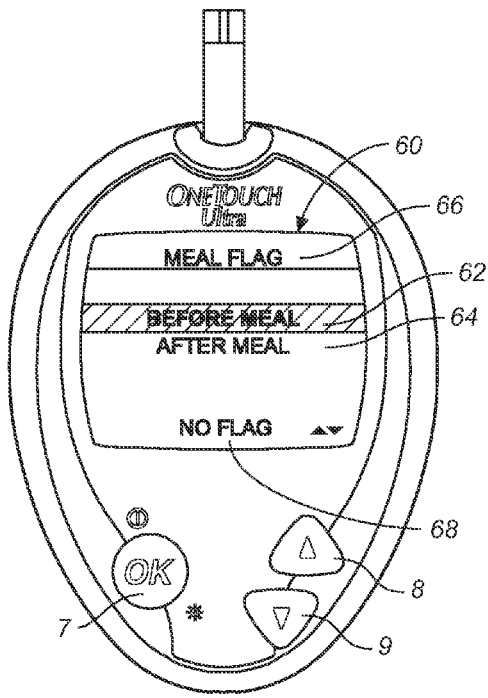
FIG. 8 is an illustration of a meal flag selection screen for a blood glucose meter, according to an embodiment of the present invention.

In respect to test result screen 40 illustrated in FIG. 7, up arrow 50 and/or down arrow 52 may blink, described as display modification indicators in relation to FIG. 3. When test result screen 40 is first displayed, up arrow 50 blinks, while down arrow 52 does not blink. This prompts the user to press up button 8 in result screen 40, directly accessing a first selected information screen containing meal flag options 60, as shown in FIG. 8. The user then uses up and down buttons 8, 9 to select either a premeal 62 or a postmeal 64 flag. Pressing OK button 7 confirms the selection and returns to the result screen, now with a meal flag added above the result as shown in FIG. 9. FIG. 9 shows a 'before meal' result screen 70 that includes a before meal flag 72. If the user selects 'after meal' (option 64 in FIG. 8), then 'before meal' flag 72 would be replaced with 'after meal'.

Returning to FIG. 7, once a meal flag has been entered, up arrow 50 stops flashing and down arrow 52 starts to blink (e.g. flash) on and off This prompts the user towards a second selected information screen. By pressing down button 9, first comment selection screen 80 is displayed, as illustrated in FIG. 10. First comment selection screen 80 includes a comment title 82, a first list of comments 84, and a first comment page number 86. First list of comments includes no comment, not enough food, too much food and mild exercise. Pressing up button 8 or down button 9 scrolls from comment to comment. If the user scrolls down, beyond the last comment in list 84, second comment selection screen 90 appears, as illustrated in FIG. 11 that may include further options such as hard exercise, medication, stress and illness. Once again, by using up button 8 and down button 9, a user may scroll from comment to comment. Scrolling up, beyond the top comment, returns the user to first comment selection screen 80, and scrolling down may take the user to a third comment selection screen (not shown) that could include comments such as feel hypo, menses, vacation and other. It would be apparent to a person skilled in the art that any number of different comment options could be included, and is not restricted to those contained herein.

Once the desired comment has been highlighted, it is selected by pressing OK button 7. This adds the comment 98 e.g. 'hard exercise' to the result screen, as illustrated in FIG. 12. Once a comment has been selected, it appears above footer area 27, and indicators 50 and 52 stop flashing. Referring again to FIG. 10, by highlighting and selecting 'no comment' 88 from first list of comments 84, the display returns to result screen 40, as illustrated in FIG. 7, whereby no comment is displayed, and any previously entered comment is removed.

Using arrows that blink and do not blink greatly simplifies the user interface, and provides a prompt or reminder to the user to enter pertinent information such as meal flags and comments that might otherwise be overlooked. Optionally, a button on the user interface may illuminate or flash to prompt the user to press it, taking them directing to a specific data entry screen. Meal flags and comments can be useful in interpreting test results, particularly by the patient's physician, and are frequently not entered in logbooks. Blinking arrows are readily noticeable, and when combined with simple and direct menu options, increase the use of meal flags and comments. It would be apparent to those skilled in the art that other techniques may also be used to attract attention to menu options, including colors, increased font size, graphic characters, and sound, to prompt the user to take certain actions and be led directly to data input screens.

FIG. 8 is an illustration of a first meal flag selection screen 60, accessible from test result screen 40 by way of up button 8. First meal flag selection screen 60 includes a before meal option 62, an after meal option 64, a meal flag title 66, and a no flag option 68. Before meal option 62, after meal option 64, and no flag option 68 can be highlighted by pressing up button 8 or down button 9, then accepting the choice using OK button 7. By pressing OK button 7, the before meal option 62 will be confirmed, and the flag is added to the result screen, as illustrated in FIG. 9. Similarly, a result can be given an after meal flag. Once a meal flag has been selected, it appears in heading area 30, illustrated in FIG. 5.

When turning the meter on by pressing OK button 7, a display check screen and a splash screen if applicable, may optionally be provided prior to displaying main menu screen 100, illustrated in FIG. 13. Main menu screen 100 includes a main menu title 102, a last result option 104, an all results option 106, a result average option 108, a set up option 110 and a meter off option 112. By using up button 8 and down button 9, the user can highlight each of the options. Once highlighted, the option is selected by pressing OK button 7. By pressing OK button 7 when last result option 104 is highlighted for example, last result option 104 is selected, and a result screen is displayed for the last test performed. The result screen that is displayed varies, depending upon the sample that was run, and whether meal flags or comments were entered. Typical result screens are illustrated in FIGS. 7, 9, and 12. While the result screen is displayed, pressing up button 8 returns the user to the first meal flag selection screen 60, where they can choose to edit the meal flag for the last result. Pressing down button 9 returns the user to first comment selection screen 80, where they can choose to edit the comment for the last result. Pressing OK button 7 while the result screen is displayed returns the user to main menu screen 100, illustrated in FIG. 13.

Figure 14:
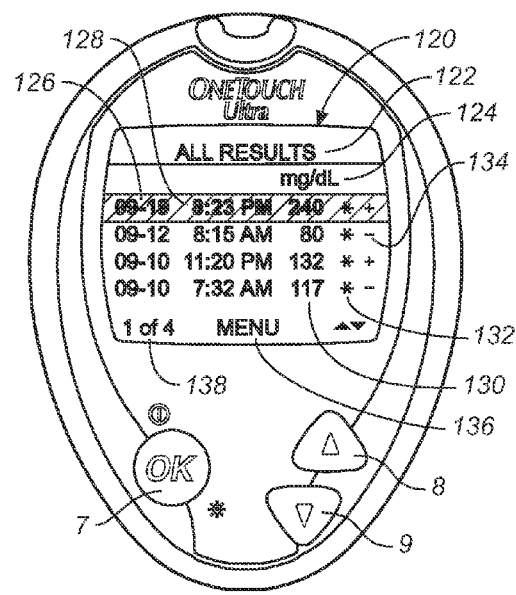
FIG. 14 is an illustration of an 'all results' screen for a blood glucose meter, according to an embodiment of the present invention.

From main menu screen 100, down button 9 can be used to highlight 'all results' option 106, as illustrated in FIG. 13. Pressing OK button 7 accepts 'all results' option 106, and displays the all results screens, an example of which is illustrated in FIG. 14. Each 'all results' screen may display up to four test results, with additional pages added, indicated by page information 138, to accommodate up to 500 test results, listed in reverse chronological order.

FIG. 14 shows an example 'all results' screen 120, including an all results title 122, a unit of measurement display 124, a test date column 126, a test time column 128, a test result column 130, a comment column 132, a meal flag column 134, a page number 138, and a menu option 136. Pressing up button 8 or down button 9 scrolls up or down, highlighting different test results. Pressing up button 8 or down button 9 for a few seconds scrolls sequentially, page by page.

Referring again to FIG. 14, an asterisk in comment column 132 indicates that the test record includes a comment. A "C" in comment column 132 indicates that the test was performed on control solution. A plus sign in meal flag column 134 indicates that the result has been flagged as after meal, while a minus sign in meal flag column 134 indicates that the result has been flagged as before meal. If OK button 7 is pressed while a result is highlighted, the result screen for that test is displayed. Typical result screens are illustrated in FIGS. 7, 9, and 12. Pressing OK button 7 while a result screen is displayed returns the user to the 'all results' screen, illustrated in FIG. 14. Pressing OK button 7 while menu option 136 is highlighted returns the user to main menu screen 100, as illustrated in FIG. 13.

Figure 15:
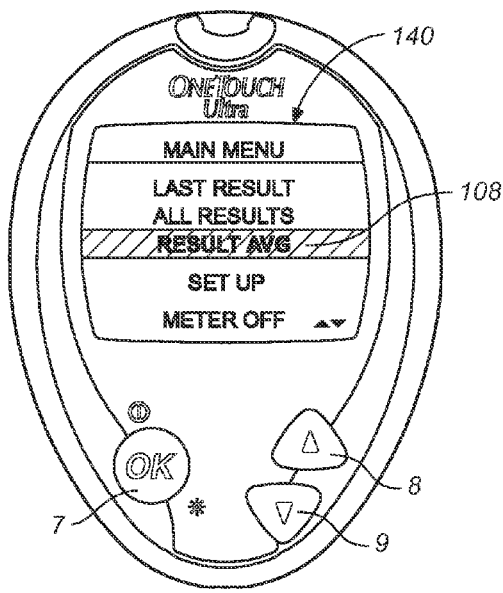
FIG. 15 is an illustration of a main menu screen for a blood glucose meter according to an embodiment of the present invention, with a 'result average' option highlighted.
Figure 16:
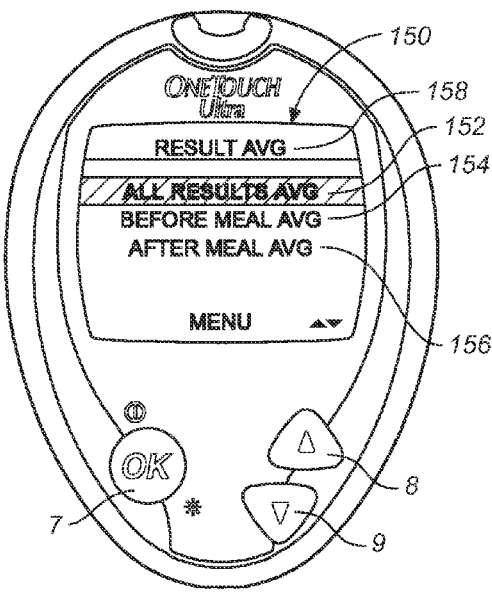
FIG. 16 is an illustration of a result average menu screen for a blood glucose meter, according to an embodiment of the present invention, showing an 'all results average' option highlighted.

To display 'result average' menu screen 150, illustrated in FIG. 16, the user highlights 'result average' option 108 in 'result average option' screen 140, illustrated in FIG. 15, then presses OK button 7. Result average menu screen 150, illustrated in FIG. 16, includes an 'all results average' option 152, a 'before meal average' option 154, an 'after meal average' option 156, and a 'result average' title 158. By using up button 8 or down button 9, the user can highlight any one of these options. The highlighted choice is accepted by pressing OK button 7.

Figure 17:
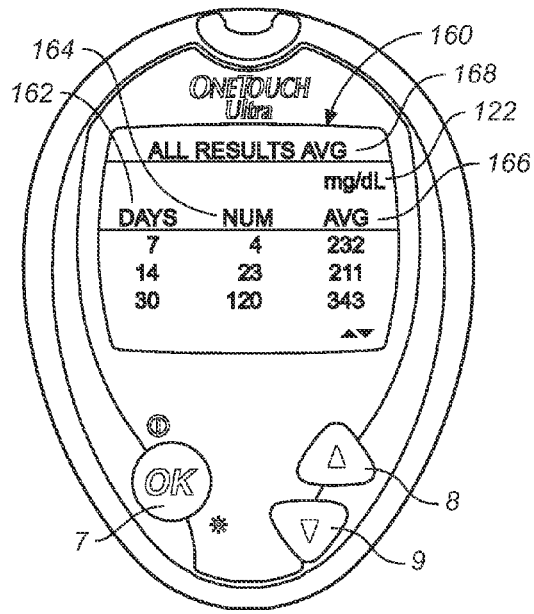
FIG. 17 is an illustration of an 'all results average' screen for a blood glucose meter, according to an embodiment of the present invention.
Figure 18:
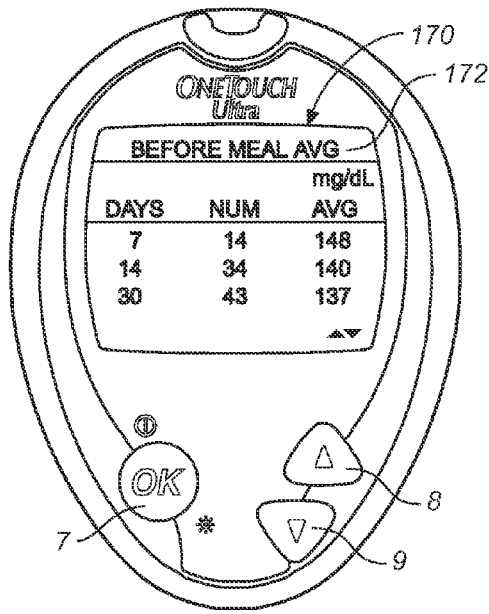
FIG. 18 is an illustration of a 'before meal average' screen for a blood glucose meter, according to an embodiment of the present invention.
Figure 19:
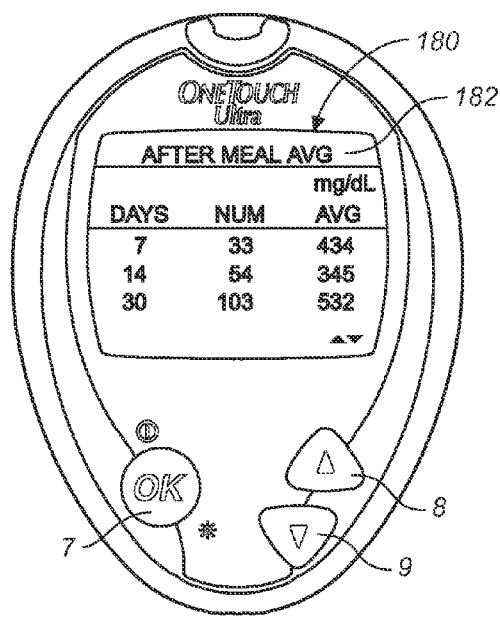
FIG. 19 is an illustration of an 'after meal average' screen for a blood glucose meter, according to an embodiment of the present invention.

By highlighting 'all results average' option 152 and pressing OK button 7, 'all results average' screen 160 is displayed, as illustrated in FIG. 17. All results average screen 160 includes a number of days column 162, a number of tests column 164, a test average column 166, and an all results average title 168. Test averages are calculated and displayed for the number of tests reported in number of tests column 164 conducted during the number of days reported in number of days column 162. Pressing OK button 7 while 'all results average' screen 160 is displayed returns the user to 'result average' menu screen 150, illustrated in FIG. 16.

From result average menu screen 150, 'before meal average' option 154 can be highlighted using up button 8 or down button 9. Pressing OK button 7 while 'before meal average' option 154 is highlighted displays 'before meal average' screen 170, illustrated in FIG. 18. Included in 'before meal average' screen 170 is 'before meal average' title 172. As was the case for 'all results average' screen 160, illustrated in FIG. 17, test averages are calculated and displayed for the number of tests reported in number of tests column 164 conducted during the number of days reported in number of days column 162. In this case, however, the test averages are based on results that have been flagged as occurring before meals. Pressing OK button 7 while 'before meal average' screen 170 is displayed returns the user to 'result average' menu screen 150, illustrated in FIG. 16.

From 'result average' menu screen 150, 'after meal average' option 156 can be highlighted using up button 8 or down button 9. Pressing OK button 7 while 'after meal average' option 156 is highlighted displays 'after meal average' screen 180, illustrated in FIG. 19. Included in 'after meal average' screen 180 is after meal average title 182. As was the case for 'all results average' screen 160, illustrated in FIG. 17, test averages are calculated and displayed for the number of tests reported in number of tests column 164 conducted during the number of days reported in number of days column 162. In this case, however, the test averages are based on results that have been flagged as occurring after meals. Pressing OK button 7 while the 'after meal average' screen 180 is displayed returns the user to 'result average' menu screen 150, illustrated in FIG. 16.

Meters currently available that do capture information such as pre-breakfast, post-breakfast, pre-lunch, post-lunch, pre-dinner and post-dinner, typically require many more steps to enter such information, and also typically calculate averages within categories such as those listed. A further advantage provided by the user interface of the present invention is the aggregation of all results as either pre- or post-meal. Such information is simpler and easier for the user to enter at the time of each test prompted by display modification indicators described herein, and is of use to the patient's health case practitioner.

Figure 20:
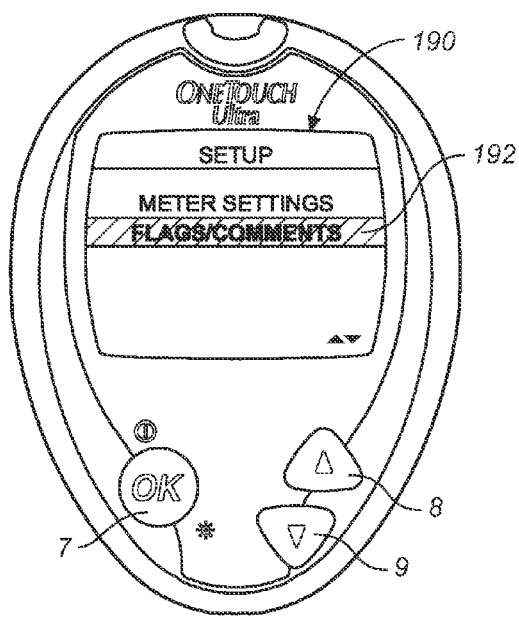
FIG. 20 is an illustration of a set up menu screen for a blood glucose meter, according to an embodiment of the present invention, showing a flags/comments option highlighted.
Figure 21:
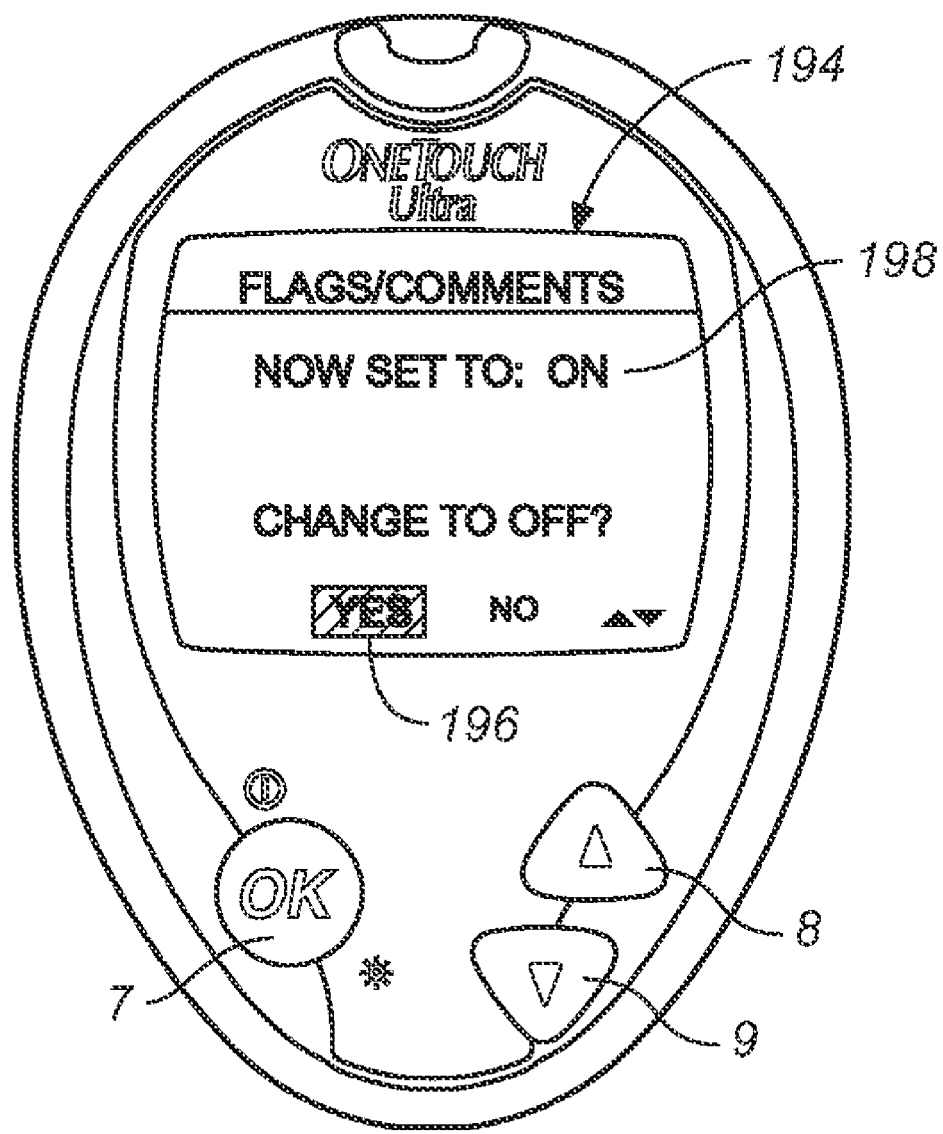
FIG. 21 is an illustration of a flags/comments option screen for a blood glucose meter, according to an embodiment of the present invention.

FIG. 20 shows an example setup menu screen 190, with a flags/comments option 192 in a highlighted state. Pressing OK button 7 while flags/comments option 192 is highlighted leads to flags/comments set up screen, shown in FIG. 21, whereby the option is provided to the user to either enable or disable the meal and/or comment flags feature. FIG. 21 shows an example flags/comments set up screen 194, with the 'accept' 196 setting highlighted. Pressing OK button 7 while option 'accept' 196 is highlighted would change the setting status 198 to off. The meal flag/comments feature can be re-enabled following the same procedure.

The invention claimed is:

1. A method of operating an analyte measurement device having a display, user interface, plurality of user interface buttons, and processor connected thereto, the method comprising:
   pressing one of the user interface buttons to enter a menu mode;
   pressing another of the user interface buttons to select the option of enabling or disabling user selectable flags;
   activating the one of the user interface buttons to confirm the selection of enabling or disabling user selectable flags;
   measuring an analyte with the analyte measurement device;
   displaying a value representative of the analyte;
   if the user selectable flag has been enabled then upon pressing the one of two user interface buttons, at least one user selectable flag is selected; and
   confirming the selection of the at least one user selectable flag with the representative value of the analyte; and
   displaying the value and the flag on the display.

2. A method of operating an anal to measurement device having a display, user interface, plurality of user interface buttons, and processor connected thereto, the method comprising:
   pressing one of the user interface buttons to enter a menu mode;
   pressing another of the user interface buttons to select the option of enabling user selectable flags;
   activating the one of the user interface buttons to confirm the selection of enabling user selectable flags, in which the activating further comprises actuating the another of the user interface buttons to turn the user selectable flag on or off;
   measuring an analyte with the analyte measurement device;
   displaying a value representative of the analyte;
   if the user selectable flag has been enabled then upon pressing the one of two user interface buttons, at least one user selectable flag is selected; and
   confirming the selection of the at least one user selectable flag with the representative value of the analyte; and
   displaying the value and the flag on the display.

3. The method of claim 1, in which the one user interface button comprises an ok button.

4. The method of claim 1, in which the another of the interface buttons comprises one of an up and a down button.

5. The method of claim 1, in which the user selectable flags comprise a before meal flag or an after meal flag.

6. The method of claim 1, in which the confirming comprises storing in a memory a date and a time at a completion of the measuring with the selected flag.

7. The method of claim 1, in which the analyte measurement device comprises a glucose meter.

8. The method of claim 1, in which the measuring comprises:
   inserting a test strip into a port provided by the analyte measurement device; and
   depositing a blood sample on a testing portion of the test strip.

9. The method of claim 8, in which the inserting comprises prompting for a calibration code specific to the test strip.

10. The method of claim 1, in which the one of the plurality of user selectable flags is selected from a group consisting essentially of at least one of a comment, a plurality of comments, comment page number, no comment, not enough food, too much food, mild exercise, strenuous exercise, medication, stress, illness, hypoglycemic state, menses, vacation, and combinations thereof.

11. The method of claim 1, in which the value comprises a glucose concentration.

* * * * *